(12) United States Patent
Amar

(10) Patent No.: US 6,494,868 B2
(45) Date of Patent: Dec. 17, 2002

(54) SET OF CANNULAE FOR TISSUE INJECTIONS IN THE HUMAN FACE

(76) Inventor: Roger E. Amar, 26 Avenue de Mazargues, 13008, Marseille (FR)

( * ) Notice: Subject to any disclaimer, the term of this patent is extended or adjusted under 35 U.S.C. 154(b) by 0 days.

(21) Appl. No.: 09/818,464

(22) Filed: Mar. 27, 2001

(65) Prior Publication Data

US 2001/0037092 A1 Nov. 1, 2001

(30) Foreign Application Priority Data

Apr. 27, 2000 (FR) .............................................. 0005401

(51) Int. Cl.⁷ .................. A61M 5/32; A61M 5/178; A61B 17/32; A61B 17/34
(52) U.S. Cl. .................. 604/273; 604/272; 604/274; 604/164.11; 606/167; 606/185
(58) Field of Search .............................. 604/19, 27, 43, 604/48, 93.01, 164.01, 164.11, 170.01, 170.03, 264, 272, 273, 274, 511, 523, 525, 533; 606/167, 170, 174–179, 181, 185; 128/919

(56) References Cited

U.S. PATENT DOCUMENTS

| | | | |
|---|---|---|---|
| 2,748,769 A | * 6/1956 | Huber | |
| 2,899,959 A | 8/1959 | Ginsburg | |
| 4,710,180 A | * 12/1987 | Johnson | 604/239 |
| 4,759,746 A | * 7/1988 | Straus | 604/51 |
| 5,207,658 A | * 5/1993 | Rosen et al. | 604/272 |
| 5,255,691 A | * 10/1993 | Otten | 607/117 |
| 5,284,476 A | 2/1994 | Koch | |
| 5,628,734 A | * 5/1997 | Hatfalvi | 604/272 |
| 6,074,367 A | * 6/2000 | Hubbell | 604/164 |
| 6,299,591 B1 | * 10/2001 | Banko | 604/22 |

FOREIGN PATENT DOCUMENTS

| | | |
|---|---|---|
| DE | 2403730 | 8/1974 |
| FR | 2143092 | 2/1973 |

* cited by examiner

Primary Examiner—Gregory Huson
Assistant Examiner—Anunadha Ramana
(74) Attorney, Agent, or Firm—Stetina Brunda Garred & Brucker

(57) ABSTRACT

A set of cannulae for tissue injections is disclosed. The cannulae are ideally suited for tissue injections in the human body. In particular, the cannulae are well-suited for muscle injections in the human face. Each cannula injecting device includes a hub attached to a tubular needle with a blunt tip or spatula-like tip. The tubular needle is curved and includes a side opening located near the tip.

41 Claims, 5 Drawing Sheets

SET OF CANNULAE FOR TISSUE INJECTIONS IN THE HUMAN FACE

CROSS-REFERENCE TO RELATED APPLICATIONS

This application claims the benefit of French Application 0005401, filed Apr. 27, 2000.

STATEMENT RE: FEDERALLY SPONSORED RESEARCH/DEVELOPMENT (Not Applicable)

BACKGROUND OF THE INVENTION

The present invention is generally directed to surgical devices, and more particularly to a set of cannulae for tissue injections in the human body, in particular, the human face.

In recent years, the fields of aesthetic and plastic surgery have opened new techniques in medicine. One of the latest techniques being used for rejuvenation and correction of scars and tissue defects is fat autografting. Prior art systems use a straight cannula for the fat micro injection in the human face. These straight cannulae are not perfectly adapted to the human face. Thus, the use of these straight cannulae in the human face causes some distortion and harm to the muscle fibers and the delicate superficial subcutaneous vascularization.

Thus, a need exists for a non-traumatic instrumentation for fat grafting and tissue restructuring in the human face.

BRIEF SUMMARY OF THE INVENTION

The present invention is directed to a set of cannulae for tissue injections in the human body, in particular, the human face. The set of cannulae includes a plurality of cannula injecting devices wherein each cannula injecting device comprises a hub (or nozzle) which has a central x-axis and a tubular needle connected to the hub wherein the tubular needle is curved and comprises a tip and a side opening located near the tip. Each cannula is curved to be suited for injections into at least one muscle of the human face.

In accordance with other aspects of the invention, the cannula injecting device is used for injections in the Orbicularis Oculii muscles and/or the nasolabial furrow. The tubular needle may be uniformly curved with the side opening looking inside the curve. The uniformly curved cannula injecting device may have a blunt tip, a working length of about 70 mm and a curve with an arc which subtends an angle of about 220.

In accordance with yet other aspects of the invention, the cannula injecting device is used for injections in the upper lip philtrum. The tubular needle may be uniformly curved with the side opening looking inside the curve. The tubular needle may have a blunt spatula-like tip, a working length of about 35 mm and an arc which subtends an angle of approximately 80°.

In accordance with still other aspects of the invention, the cannula injecting device may be used for injections in the Zygomatic Major and/or Zygomatic Minor muscles in the malar area. The tubular needle of the cannula injecting device may have a straight portion connected to the hub followed by a uniformly curved portion. The side opening may look inside the curve. The cannula injecting device may have a working length of about 70 mm, with the straight portion having a length of about 15 mm and the curve portion having a length of about 55 mm and an arc which subtends an angle of approximately 20°.

In accordance with further aspects of the invention, the cannula injecting device may be used for injections in the Procerus muscle, the Corrugator muscle, the Nasalis muscle, the Frontal muscle and glabellar angle and/or the mandibular angles. The cannula injecting device may have a tubular needle with a straight portion connected to the hub, followed by a curved portion. The cannula injecting device may have the side opening looking outside the curve of the curved portion. The cannula injecting device may have a working length of about 70 mm, with the straight portion having a length of about 55 mm and the curved portion having a length of about 15 mm and an arc which subtends an angle of about 6°.

In accordance with still further aspects of the invention, the cannula injecting device may be used for injections in the Orbicularis Oris muscle and the Buccinator muscle. The tubular needle of the cannula injecting device may have a straight portion connected to the hub, followed by a curved portion. The tubular needle may have a side opening looking inside the curve of the curved portion. The cannula injecting device may have a working length of about 70 mm, with a straight portion having a length of about 5 mm and the curved portion having a length of about 65 mm and an arc which subtends an angle of approximately 34°.

In accordance with yet further aspects of the invention, the cannula injecting device may be used for injections in the Mentalis muscle, the Depressor Labii Inferioris muscle and the Depressor Anguli Oris muscle and/or the mandibular rim. The tubular needle may have a double curve which includes a first curve connected to the hub, followed by a reverse curve and a straight portion. The straight portion includes the side opening. The side opening may look inside the reverse curve. The first curve of the cannula injecting device may have a length of about 25 mm and an arc which subtends an angle of approximately 9°, the reverse curve and the straight portion have a total length of about 25 mm and an arc which subtends an angle of approximately 26°.

In accordance with other aspects of the invention, the cannula injecting device may be used for injections in a cheek portion of the Platysma muscle, and a cheek-pillar, and/or a lower lip-pillar. The tubular needle has a straight portion substantially parallel to the x-axis of the hub, the first curve may have a length of about 18 mm and an arc which subtends an angle of about 107°, the reverse curve has a length of about 7 mm and an arc which subtends an angle of about 20° and the straight portion has a length of about 30 mm.

In accordance with further aspects of the invention, the cannulae may be grouped into sets.

BRIEF DESCRIPTION OF THE SEVERAL VIEWS OF THE DRAWING

These as well as other features of the present invention will become more apparent upon reference to the drawings wherein.

DETAILED DESCRIPTION OF THE INVENTION

Scar defects and aging deformations are linked, to a certain degree, to the atrophy of the human musculature. The present invention is directed to a non-traumatic instrumentation for injection into the muscles of the human face in order to correct this atrophy. In exemplary embodiments of the invention, a set of cannulae is used for the injection of appropriate biological material during face surgery. The cannulae of the present invention allow for muscle injections to be made lengthwise along the pathway of the muscle fibers, that is, the lengthway of the arteries, veins and lymphatic vessels of the human face. The cannulae follow the length of the muscle from its origin to its insertion, that is, from the bone to the deep dermis or vice versa. The present invention allows micro injection to be made easily into the muscle core. The curvatures of the cannulae of the present invention are well adapted to the facial skeleton which makes subperiosteum injections easier. In addition, the angles of the cannulae of the present invention avoid any distortion in the direction of the injections.

FIGS. 1–5 illustrate the muscular structure of the human face. FIGS. 6–12 illustrate cannulae designed for specific muscles in the human face as described in future detail below. Each of the cannulae include a tubular needle with a tip (46 in FIG. 6) and a side opening 48 close to the tip. Some of the cannulae have a blunt tip and some of the cannulae have a blunt spatula-like tip. Preferably, the length of the tubular needle is between 40 and 80 mm with an external diameter of about 1.5 mm. Preferably, each of the cannulae is made out of stainless steel, titanium or any material suitable for sterilization with an autoclave, such as hard plastic.

Figure 1:
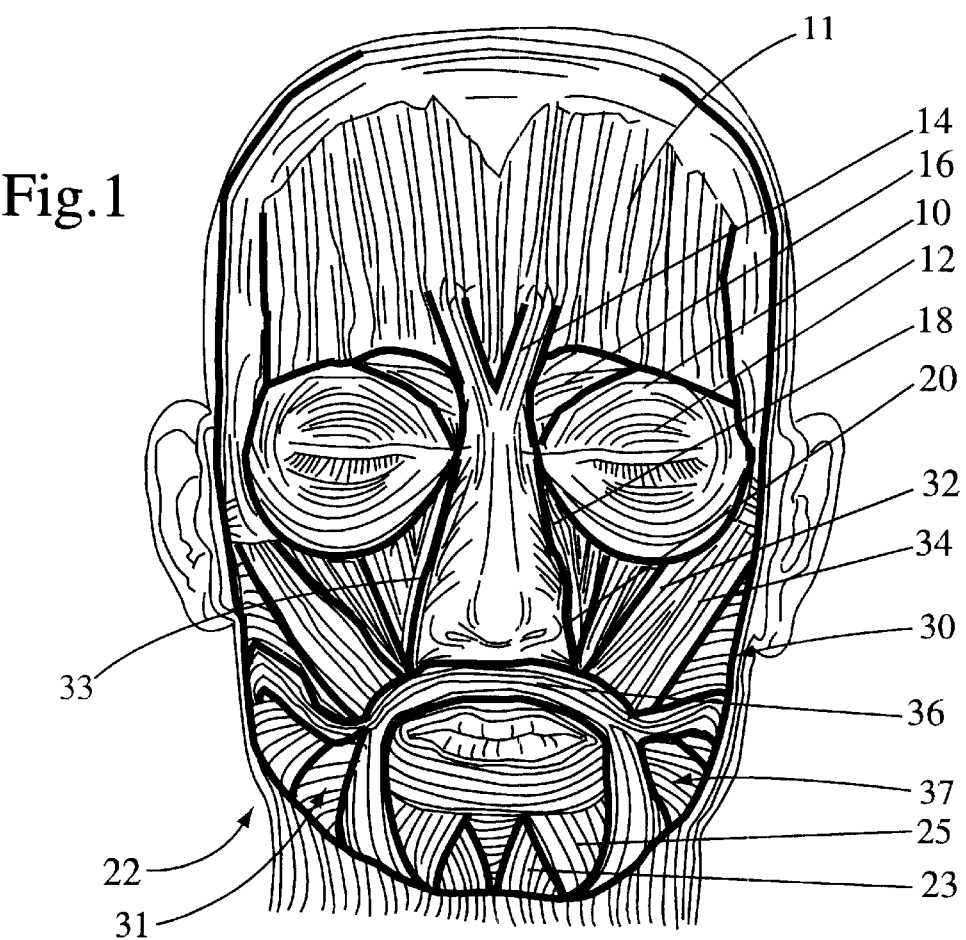
FIGS. 1–3 are front perspective views of the muscular structure of the human face.
Figure 4:
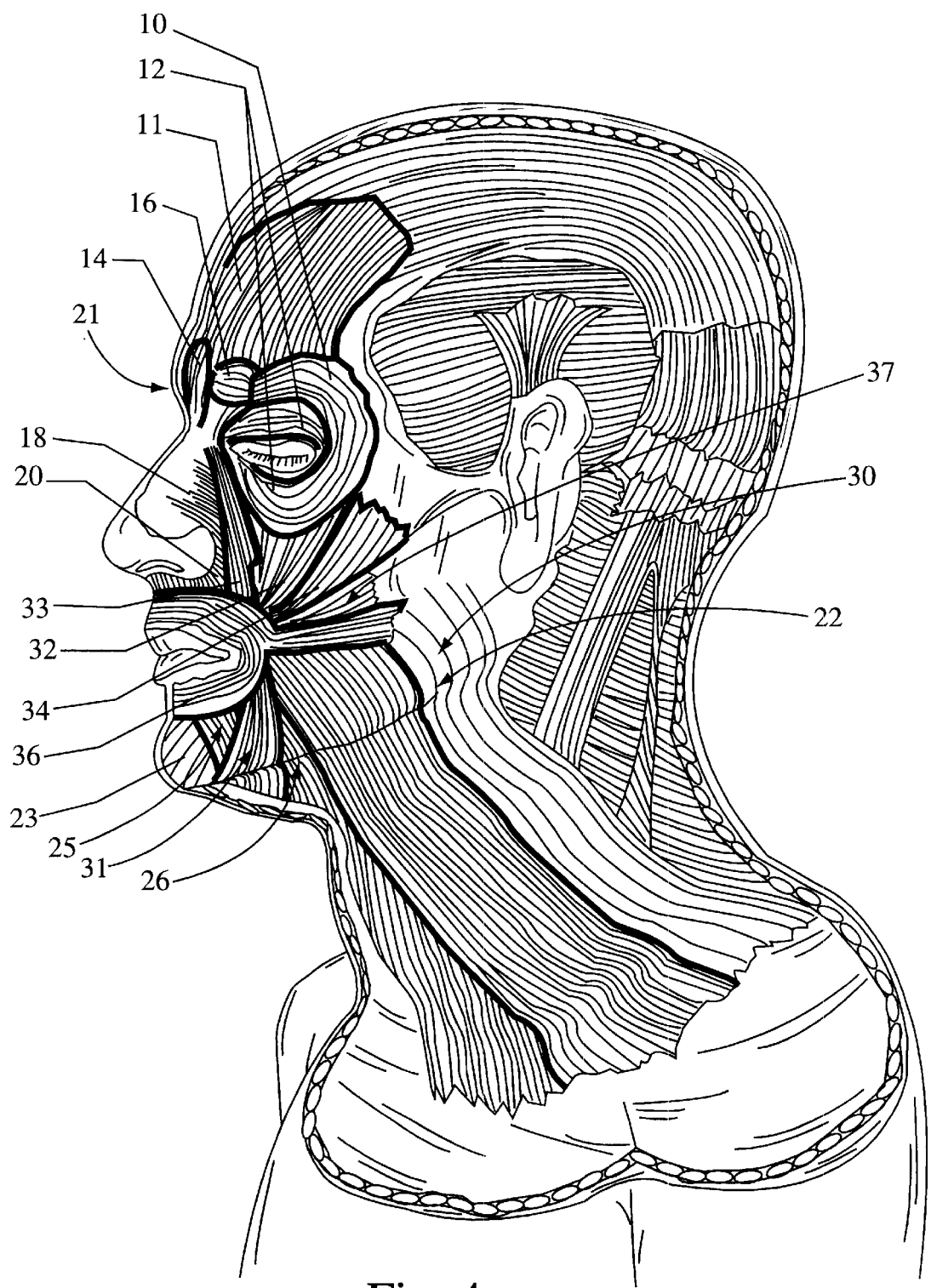
FIG. 4 is a side perspective view of the muscular structure of a human face.
Figure 6:
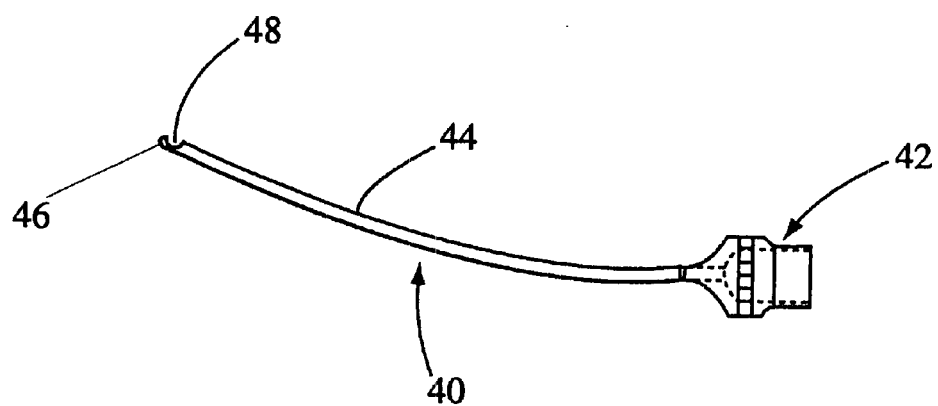
FIG. 6 is a side view of a cannula for Orbicularis Oculii muscle injections formed in accordance with the present invention.

FIG. 6 shows a uniformly curved cannula 40 which is ideally suited for injections in the Orbicularis Oculii muscles. The Orbicularis Oculii muscles include an Orbital part 10 and a Palpebral part 12 as shown in FIGS. 1 and 4. Cannula 40 provides a surgeon with the capacity to follow the Orbital rim 15 and the eyebrow curvature 17 shown in FIG. 5. Cannula 40 can also be used in the nasolabial furrow 19 shown in FIG. 2 with minimum trauma to the surrounding tissues.

Cannula 40 shown in FIG. 6 includes an adaptable hub 42 which is used for luer lock syringe fixation. The hub 42 bears a uniformly curved tubular needle 44 with a blunt tip 46 and a side opening 48 close to the tip looking inside the curve. Preferably, the cannula 40 has an arc which subtends an angle of approximately 22°. Preferably, the external diameter of the tubular needle 44 is about 1.5 mm and the opening 48 of the cannula is about 2.5 mm in length. It will be appreciated that other diameters can be used. A smaller diameter needle is preferable so that trauma to the facial tissue is minimized. Preferably, the working length of the cannula 40 is about 70 mm. As used herein, "working length" defines the distance between the blunt tip 46 and the adaptable hub 42. In other words, the working length is the length of the tubular needle 44 or the entire length of the cannula 40 minus the length of the adaptable hub 42. Preferably, the diameter of the working length is constant.

FIGS. 7–12 illustrate other cannulae ideally suited for various facial muscles as described below. The cannulae shown in FIGS. 7–12 are similar in structure to cannula 40 shown in FIG. 6 but with varying shapes and sizes as described below.

Figure 7:
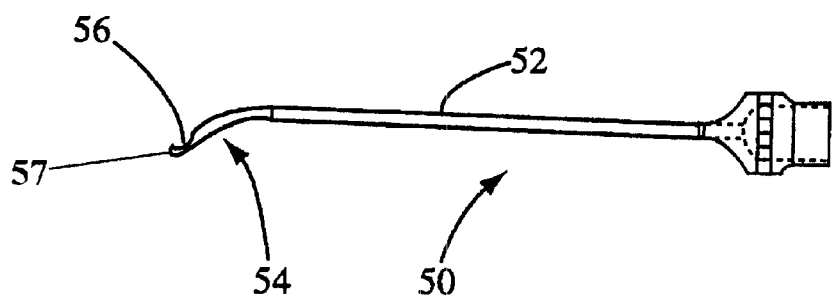
FIG. 7 is a side view of a cannula for Procerus muscle and Corrugator muscle injections formed in accordance with the present invention.

FIG. 7 shows a cannula 50 which begins with a straight portion 52 and ends with a curved portion 54 and is ideally suited for injections in the Procerus 14 muscle, as well as the Corrugator 16 and Nasalis muscles. The Nasalis muscles include a transverse part 18 and an alar part 20. Cannula 50 enables a surgeon to inject the Frontal muscle 11 and glabellar angle 21 (shown in FIG. 4). Cannula 50 could also be used in the mandibular angles 22 (shown in FIG. 1). Preferably, cannula 50 has a working length of about 70 mm with the straight portion 52 having a length of about 55 mm and the curved portion 54 having a length of about 15 mm and an arc which subtends an angle of about 6°. Side opening 56 is close to the tip 57 looking outside the curve. Preferably, cannula 50 has a blunt spatula-like tip 57.

Figure 8:
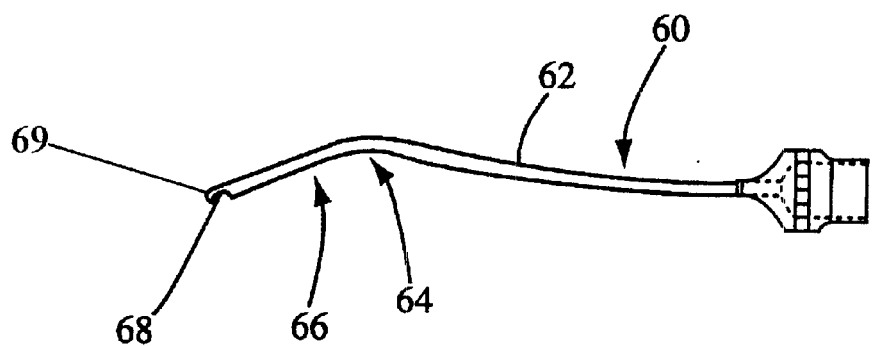
FIG. 8 is a side view of a cannula for Mentalis muscle, Depressor Labii Inferioris muscle and Depressor Anguli Oris muscle injections formed in accordance with the present invention.

FIG. 8 shows a cannula 60 with a double curvature which is ideally suited for injections of the Mentalis 23 and the Depressor Labii Inferioris muscles 25, and Depressor Anguli Oris muscle 31. Cannula 60 enables a surgeon to inject into the mandibular rim 26 and the chin. Cannula 60 can also be used for injecting the marionette furrow 27 in the lower portion of the mouth angle. Cannula 60 begins with curve 62 followed by a reverse curve 64 and ends with a straight portion 66. Preferably, the working length of cannula 60 is about 50 mm with the curve 62 having a length of about 25 mm and an arc which subtends an angle of approximately 9°, and the reverse curve 64 and the straight portion 66 having a total length of about 25 mm and an arc which subtends an angle of approximately 26°. Side opening 68 of the cannula 60 is close to the tip 69 looking inside the last curve (i.e., reverse arc 64). Preferably, the tip 69 is a blunt spatula-like tip.

Figure 9:
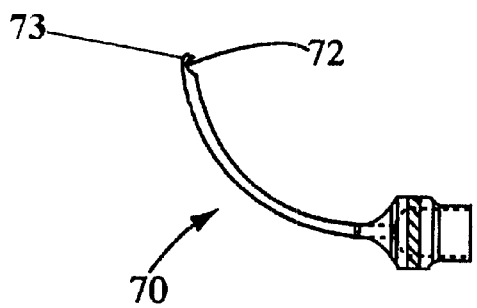
FIG. 9 is a side view of a cannula for Philtrum, Levator Labii muscle and Temporal Fossa injections formed in accordance with the present invention.

FIG. 9 shows a cannula 70 which is uniformly curved, but which is shorter than the other cannulae of the present invention. Cannula 70 is ideally suited for injections of the upper lip Philtrum 13 shown in FIG. 3, and insertions of the Levator Labii muscle 33 shown in FIGS. 1 and 4. Preferably, cannula 70 has an arc which subtends an angle of approximately 80°, and a blunt spatula-like tip 73 with a side opening 72 close to the tip 73 and looking inside the curve. Preferably, cannula 70 has a working length of about 35 mm.

Figure 2:
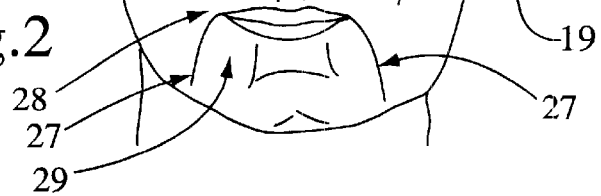
Figure 3:
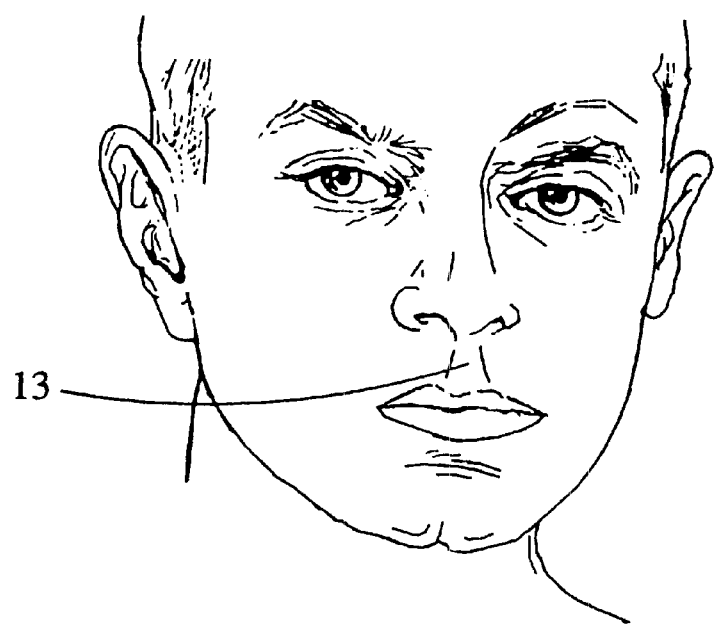
Figure 5:
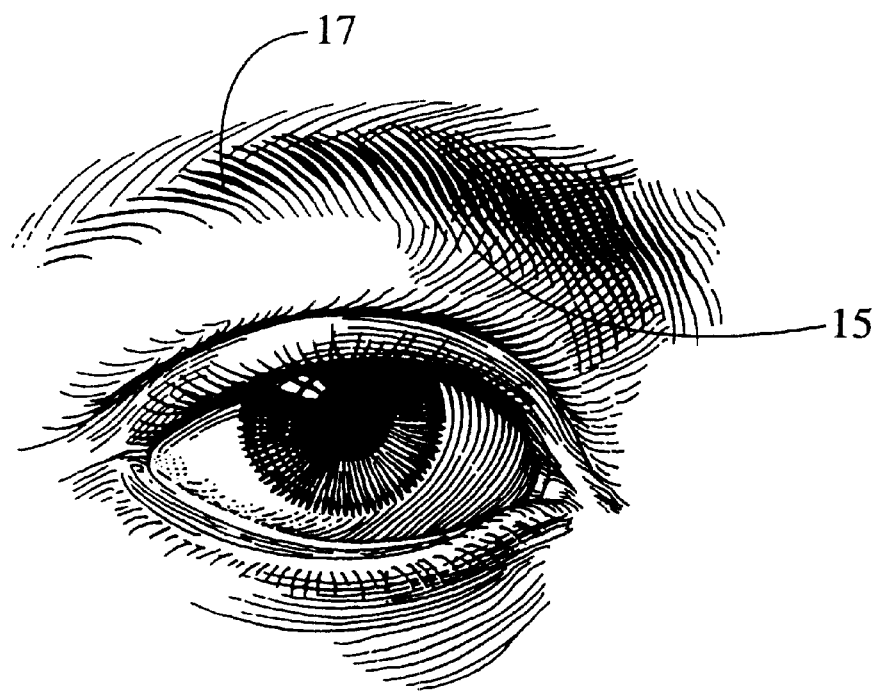
FIG. 5 is a front perspective view of the muscular structure of the eye area of the human face.
Figure 10:
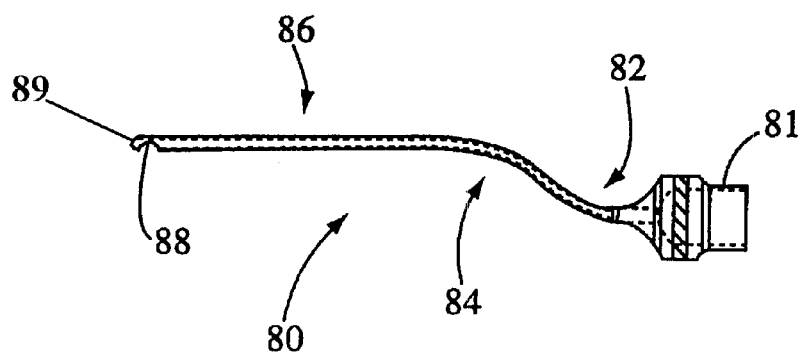
FIG. 10 is a side view of a cannula for Platysma muscle injections formed in accordance with the present invention.

FIG. 10 shows a cannula 80 which has a bayonet-like shape and is ideally suited for injections in the cheek portion of the Platysma muscle 30. Due to the bayonet-like shape, cannula 80 can be used in many regions of the face, for example, in the cheek pillar 28 or lower lip pillar 29, as shown in FIG. 2. Cannula 80 shown in FIG. 10 begins with a first curve 82 followed by a reverse curve 84 and ending with a straight portion 86 which is substantially parallel to the x-axis of the adaptable hub 81. Preferably, the working length is about 55 mm, with the first curve 82 being about 18 mm in length and having an arc which subtends an angle of approximately 69°, and the reverse curve 84 being about 7 mm in length and having an arc which subtends an angle of approximately 20°, and the straight portion being about 30 mm in length. The side opening 88 close to the tip 89 is looking inside the reverse curve 84. Preferably, the tip 89 of the cannula 80 is blunt.

Figure 11:
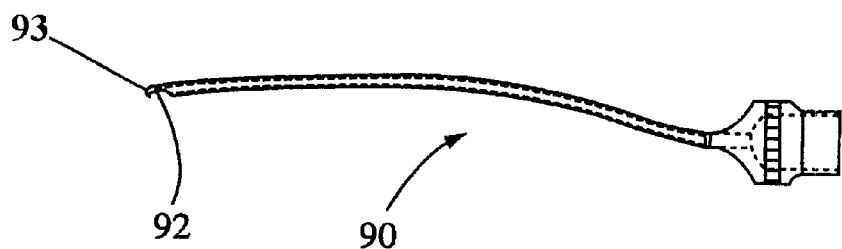
FIG. 11 is a side view of a cannula for Zygomatic Minor and Major muscle injections formed in accordance with the present invention.

Cannula 90 shown in FIG. 11 is ideally suited for injecting the Zygomatic Minor 32 and Major 34 muscles in the malar area. Preferably, cannula 90 is uniformly curved after a short straight portion of 15 mm and has an arc which subtends an angle of approximately 20°. The side opening 92 is close to the blunt spatula-like tip 93 looking inside the curve. Preferably, the working length of cannula 90 is 70 mm.

Figure 12:
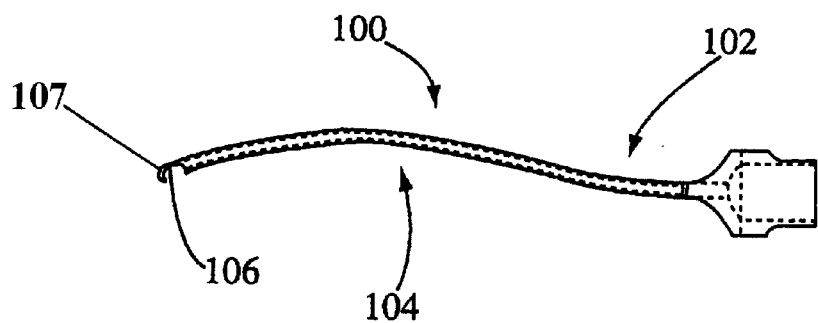
FIG. 12 is a side view of a cannula for Orbicularis Oris muscle and Depressor Anguli Oris muscle injections formed in accordance with the present invention.

Cannula 100 shown in FIG. 12 is ideally suited for Orbicularis Oris muscle and Buccinator muscle injections. The Orbicularis Oris Muscle 36 is the thick muscle which forms the bulk of the lips, and the Buccinator muscle 37 is the flat muscle which forms the bulk of the cheeks. Cannula 100 begins with a straight portion 102 which is followed by a curved portion 104. Preferably, the working length of cannula 100 is about 70 mm with the straight portion 102 having a length of about 5 mm, and the curved portion having a length of about 65 mm and an arc which subtends an angle of approximately 34°. Side opening 106 is close to the blunt tip 107 and is looking inside the curve.

Seven different cannulae suited for injections in various face muscles are described above. In exemplary embodiments of the invention, kits are created with various combinations of the cannulae. For example, a basic set is composed of the cannulae 40, 50 and 60 shown in FIGS. 6–8. This set or kit allows a surgeon to perform injections in practically all facial regions with minimum trauma, avoiding the tearing of muscle fibers and distortions in the direction of injection.

A better kit includes the cannulae 40, 50 and 60 of the basic kit described above plus cannulae 70 and 80 shown in FIGS. 9 and 10. A complete kit includes all of the cannulae of the better kit just described plus cannulae 90 and 100 shown in FIGS. 11 and 12. It will be appreciated that kits of other combinations are possible.

Additional modifications and improvements of the present invention may also be apparent to those of ordinary skill in the art. Thus, the particular combination of parts described and illustrated herein is intended to represent only a certain embodiment of the present invention and is not intended to serve as a limitation of alternative devices within the spirit and scope of the invention.

What is claimed is:

1. A cannula injecting device, comprising:
    a hub having a central x-axis; and
    a tubular needle connected to the hub, at least part of the tubular needle being curved for tissue injection in at least one specific facial muscle, the tubular needle comprising:
        a blunt tip; and
        a side opening located near the blunt tip.

2. The cannula injecting device of claim 1, wherein the tubular needle is uniformly curved and the side opening looks inside the curve of the tubular needle.

3. The cannula injecting device of claim 2, wherein the cannula injecting device is used for injections in Orbicularis Oculii muscles.

4. The cannula injecting device of claim 2, wherein the cannula injection device is used for injections in a nasolabial furrow.

5. The cannula injecting device of claim 2, wherein the cannula injecting device has a working length of about 70 mm and an arc which subtends an angle of about 22°.

6. The cannula injecting device of claim 2, wherein the cannula injecting device is used for injections in an upper lip philtrum.

7. The cannula injection device of claim 2, wherein the cannula injecting device is used for injections in Levator Labii muscles.

8. The cannula injecting device of claim 2, wherein the cannula injecting device has a blunt spatula-like tip, a working length of about 35 mm and an arc which subtends an angle of approximately 80°.

9. The cannula injecting device of claim 1, wherein the tubular needle begins with a straight portion followed by a uniformly curved portion, the side opening looks inside the curve of the tubular needle and the tip is a blunt spatula-like tip.

10. The cannula injecting device of claim 9, wherein the cannula injecting device is used for injections in the Zygomatic Minor muscle in the malar area.

11. The cannula injecting device of claim 9, wherein the cannula injecting device is used for injections in the Zygomatic Major muscle in the malar area.

12. The cannula injecting device of claim 9, wherein the straight portion is about 15 mm, the uniformly curved portion is about 55 mm and has an arc which subtends an angle of about 20°.

13. The cannula injecting device of claim 1, wherein the tubular needle begins with a straight portion followed by a uniformly curved portion, the side opening looks outside the curve of the curved portion, and the tip is a blunt spatula-like tip.

14. The cannula injecting device of claim 13, wherein the cannula injecting device is used for injections in the Procerus muscle.

15. The cannula injecting device of claim 13, wherein the cannula injecting device is used for injections in a Corrugator muscle.

16. The cannula injecting device of claim 13, wherein the cannula injecting device is used for injections in a Nasalis muscle.

17. The cannula injecting device of claim 13, wherein the cannula injecting device is used for injections in a Frontal muscle.

18. The cannula injecting device of claim 13, wherein the cannula injecting device is used for injections in a glabellar angle.

19. The cannula injecting device of claim 13, wherein the cannula injecting device is used for injections in mandibular angles.

20. The cannula injecting device of claim 13, wherein the cannula injecting device has a working length of about 70 mm, the straight portion has a length of about 55 mm, and the curved portion has a length of about 15 mm and an arc which subtends an angle of about 6°.

21. The cannula injecting device of claim 1, wherein the tubular needle begins with a straight portion followed by a uniformly curved portion, the side opening looking inside the curve of the tubular needle.

22. The cannula injecting device of claim 21, wherein the cannula injecting device is used for injections in an Orbicularis Oris muscle.

23. The cannula injecting device of claim 21, wherein the cannula injecting device is used for injections in a Buccinator muscle.

24. The cannula injecting device of claim 21, wherein the cannula injecting device has a working length of about 70 mm, the straight portion has a length of about 5 mm and the curved portion has a length of about 65 mm and an arc which subtends an angle of approximately 34°.

25. The cannula injecting device of claim 1, wherein the tubular needle comprises a double curve having a curve, a reverse curve, and a straight portion with the side opening looking inside the reverse curve.

26. The cannula injecting device of claim 25, wherein the cannula injecting device is used for injections in a Mentalis muscle.

27. The cannula injecting device of claim 25, wherein the cannula injecting device is used for injections in a Depressor Labii Inferioris muscle.

28. The cannula injecting device of claim 25, wherein the cannula injecting device is used for injections in a Depressor Anguli Oris muscle.

29. The cannula injecting device of claim 25, wherein the cannula injecting device is used for injections in a mandibular rim.

30. The cannula injecting device of claim 25, wherein the cannula injecting device is used for injections in a chin.

31. The cannula injecting device of claim 25, wherein the cannula injecting device is used for injections in a marionette furrow in a lower portion of a mouth angle.

32. The cannula injecting device of claim 25, wherein the curve has a length of about 25 mm and an arc which subtends an angle of about 9°, the reverse curve and the straight portion have a total length of about 25 mm and an arc which subtends an angle of about 26°.

33. The cannula injecting device of claim 25, wherein the cannula injecting device is used for injections in a cheek portion of a Platysma muscle.

34. The cannula injecting device of claim 25, wherein the cannula injecting device is used for injections in a cheek pillar.

35. The cannula injecting device of claim 25, wherein the cannula injecting device is used for injections in a lower lip pillar.

36. The cannula injecting device of claim 25, wherein the straight portion is substantially parallel to the x-axis of the hub, and wherein the curve has a length of about 8 mm and an arc which subtends an angle of about 69°, the reverse curve has a length of about 7 mm and an arc which subtends an angle of about 20°, and the straight portion has a length of about 30 mm.

37. A cannula set, comprising a plurality of cannula injecting devices, each cannula injecting device comprising:
   a hub having a central x-axis; and
   a tubular needle connected to the hub, wherein at least part of the tubular needle is curved for tissue injection in at least one specific facial muscle, the tubular needle comprising:
      a blunt tip; and
      a side opening located near the blunt tip.

38. The cannula set of claim 37, wherein the plurality of cannula injecting devices comprises:
   a first cannula injecting device, wherein the tubular needle is uniformly curved, the side opening looks inside the curve of the tubular needle, the first cannula injecting device has working length of about 70 mm and an arc which subtends an angle of about 22°;
   a second cannula injecting device, wherein the tubular needle has a blunt spatula-like tip and has a straight portion connected to the hub followed by a curved portion, the side opening looks outside the curve of the curved portion of the tubular needle of the second cannula injecting device, the second cannula injecting device has a working length of about 70 mm, the straight portion of the tubular needle of the second cannula injecting device has a length of about 55 mm, and the curved portion of the tubular needle of the second cannula injecting device has a length of about 15 mm and an arc which subtends an angle of about 6°; and
   a third cannula injecting device, wherein the tubular needle has a blunt spatula-like tip and a double curve, the double curve having a curve, a reverse curve, and a straight portion, the side opening looking inside the reverse curve of the tubular needle of the third cannula injecting device, the curve of the tubular needle of the third cannula injecting device having a length of about 25 mm and an arc which subtends an angle of about 9°, the reverse curve of the tubular needle of the third cannula injecting device and the straight portion of the tubular needle of the third cannula injecting device having a total length of about 25 mm and an arc which subtends an angle of about 26°.

39. The cannula set of claim 38, further comprising:
   a fourth cannula injecting device, wherein the tubular needle has a blunt spatula-like tip and is uniformly curved, the side opening looks inside the curve of the tubular needle of the fourth cannula injecting device, the fourth cannula injecting device having a working length of about 35 mm and an arc which subtends an angle of approximately 80°; and
   a fifth cannula injecting device, wherein the tubular needle has a double curve, the double curve having a curve, a reverse curve, and a straight portion with the side opening looking inside the reverse curve, the straight portion being substantially parallel to the x-axis of the hub, the curve of the tubular needle of the fifth cannula injecting device having a length of about 18 mm and an arc which subtends an angle of about 69°, the reverse curve of the tubular needle of the fifth cannula injecting device having a length of about 7 mm and an arc which subtends an angle of about 20°, and the straight portion of the tubular needle of the fifth cannula injecting device having a length of about 30 mm.

40. The cannula set of claim 39, further comprising:
   a sixth cannula injecting device, wherein with the tubular needle has a blunt spatula-like tip and a straight portion connected to the hub followed by a uniformly curved portion, the side opening looking inside the uniformly curved portion of the tubular needle of the sixth cannula injecting device, the sixth cannula injecting device having a working length of about 70 mm, with the straight portion having a length of about 15 mm and the tubular needle of the sixth cannula injecting device having an arc which subtends an angle of about 20°; and
   a seventh cannula injecting device, wherein with the tubular needle has a straight portion connected to the hub followed by a curved portion, the side opening looking inside the curve of the curved portion of the tubular needle of the seventh cannula injecting device, the seventh cannula injecting device having a working length of about 70 mm, the straight portion having a length of about 5 mm and the curved portion having a length of about 65 mm and an arc which subtends an angle of approximately 34°.

41. A method for injecting biological material into a human face, the method comprising:

(a) determining a facial muscle for receiving the injection of biological material, the muscle having a pathway of muscle fibers;

(b) selecting a cannula specifically configured for injection into the facial muscle, the selected cannula having a blunt tip and a size and curvature such that insertion of the cannula into the facial muscle and injection of the biological material into the facial muscle can be done without trauma;

(c) inserting the cannula lengthwise into the facial muscle along the pathway of muscle fibers; and (d) injecting the biological material into the facial muscle.

* * * * *